United States Patent [19]
Dodge et al.

[11] Patent Number: 5,626,563
[45] Date of Patent: May 6, 1997

[54] IRRIGATION SYSTEM WITH TUBING CASSETTE

[75] Inventors: Larry H. Dodge, River Falls, Wis.; Ulf B. Dunberger, Portsmouth, N.H.; Thomas D. Egan, Marblehead, Mass.; Harpreet Kaur, Woodbury, Minn.; Kenneth E. Merte, Saline, Mich.

[73] Assignee: Minnesota Mining and Manufacturing Company, St. Paul, Minn.

[21] Appl. No.: 371,011

[22] Filed: Jan. 11, 1995

Related U.S. Application Data

[63] Continuation of PCT/US94/00563, Jan. 12, 1994, which is a continuation-in-part of Ser. No. 3,475, Jan. 12, 1993, Pat. No. 5,403,277.

[30] Foreign Application Priority Data

Jan. 12, 1994 [EP] European Pat. Off. ............ 94 906653

[51] Int. Cl.$^6$ ...................................................... A61M 1/00
[52] U.S. Cl. ........................... 604/153; 604/30; 417/474; 417/477.9
[58] Field of Search ..................... 417/474, 476, 417/477.2, 477.9; 604/30, 34, 35, 118, 119, 153

[56] References Cited

U.S. PATENT DOCUMENTS

| | | | |
|---|---|---|---|
| D. 204,134 | 3/1966 | Duncan | D17/6 |
| D. 342,312 | 12/1993 | Pastrone et al. | D24/111 |
| D. 367,323 | 2/1996 | Carr et al. | D24/111 |
| 3,597,124 | 8/1971 | Adams | 417/477 |
| 3,900,022 | 8/1975 | Widran | 128/7 |
| 3,927,955 | 12/1975 | Spinosa et al. | 417/477 |
| 3,986,956 | 10/1976 | Anno | 210/137 |
| 3,990,444 | 11/1976 | Vial | 128/214 F |
| 4,011,940 | 3/1977 | Neal et al. | 206/1.5 |
| 4,180,074 | 12/1979 | Murry et al. | 128/276 |
| 4,187,057 | 2/1980 | Xanthopoulos | 417/63 |
| 4,210,138 | 7/1980 | Jess et al. | 128/214 E |
| 4,256,437 | 3/1981 | Brown | 417/45 |
| 4,263,909 | 4/1981 | Bush | 128/215 |
| 4,275,726 | 6/1981 | Schael | 128/213 A |
| 4,380,326 | 4/1983 | Norton | 604/151 |
| 4,425,113 | 1/1984 | Bilstad | 604/6 |

(List continued on next page.)

FOREIGN PATENT DOCUMENTS

| | | | |
|---|---|---|---|
| 0120284 | 10/1984 | European Pat. Off. | |
| 0185658B1 | 7/1986 | European Pat. Off. | |
| 0329599B1 | 8/1989 | European Pat. Off. | |
| 362822 | 4/1990 | European Pat. Off. | |
| 529902 | 3/1993 | European Pat. Off. | |
| 2513884 | 4/1983 | France. | |
| 3338758A1 | 5/1985 | Germany. | |
| WO86/00534 | 1/1986 | WIPO. | |
| WO86/01390 | 3/1986 | WIPO. | |
| WO91/15149 | 10/1991 | WIPO. | |
| 91/15149 | 10/1991 | WIPO | 604/30 |
| WO93/19791 | 10/1993 | WIPO. | |
| WO94/15658 | 7/1994 | WIPO. | |

OTHER PUBLICATIONS

"Arthro–Automat 5002", brochure of F.M. Wiest Kg, Munich, Germany, 4 pages, undated.
"Arthrocombi 5003", brochure of F.M. Wiest Kg, Munich, Germany, 4 pages, undated.

(List continued on next page.)

Primary Examiner—Robert A. Clarke
Attorney, Agent, or Firm—Gary L. Griswold; Walter N. Kirn; Stephen W. Bauer

[57] ABSTRACT

The present invention provides a tubing set in cassette form and an irrigation system employing the cassette and tubing set for use in endoscopic procedures. The tubing set includes a generally arcuate cassette which is inserted into the pump housing to effect a change in tubing sets between procedures. A valve assembly and flattened tubing segment are preferably used to provide pressure control/relief in the tubing set/irrigation system. Also provided in combination with the preferred cassette is a fitting for coupling a pressure monitoring line with pressure monitoring equipment in the irrigation system.

49 Claims, 10 Drawing Sheets

U.S. PATENT DOCUMENTS

| | | | |
|---|---|---|---|
| 4,445,826 | 5/1984 | Tarr | 417/476 |
| 4,515,584 | 5/1985 | Abe et al. | 604/66 |
| 4,526,515 | 7/1985 | DeVries | 417/63 |
| 4,537,561 | 8/1985 | Xanthopoulos | 417/63 |
| 4,552,516 | 11/1985 | Stanley | 417/477 |
| 4,604,089 | 8/1986 | Santangelo et al. | 604/30 |
| 4,631,008 | 12/1986 | Stenner | 417/477 |
| 4,637,813 | 1/1987 | DeVries | 604/6 |
| 4,650,462 | 3/1987 | DeSatnick et al. | 604/30 |
| 4,674,500 | 6/1987 | DeSatnick et al. | 128/305 |
| 4,713,051 | 12/1987 | Steppe et al. | 604/30 |
| 4,733,662 | 3/1988 | DeSatnick et al. | 128/305 |
| 4,735,558 | 4/1988 | Kienholz et al. | 417/477 |
| 4,781,687 | 11/1988 | Wall | 604/118 |
| 4,798,580 | 1/1989 | DeMeo et al. | 604/30 |
| 4,813,855 | 3/1989 | Leveen et al. | 417/477 |
| 4,820,265 | 4/1989 | DeSatnick et al. | 604/30 |
| 4,842,584 | 6/1989 | Pastrone | 604/50 |
| 4,848,338 | 7/1989 | DeSatnick et al. | 128/303 R |
| 4,902,277 | 2/1990 | Mathies et al. | 604/67 |
| 4,940,457 | 7/1990 | Olson | 604/30 |
| 4,973,311 | 11/1990 | Iwakoshi et al. | 604/119 |
| 4,998,914 | 3/1991 | Wiest et al. | 604/67 |
| 5,000,733 | 3/1991 | Mathies et al. | 604/67 |
| 5,006,109 | 4/1991 | Douglas et al. | 604/26 |
| 5,037,386 | 8/1991 | Marcus et al. | 604/43 |
| 5,044,902 | 9/1991 | Malbec | 417/477 |
| 5,057,278 | 10/1991 | Maxwell et al. | 422/81 |
| 5,082,429 | 1/1992 | Soderquist et al. | 417/477 |
| 5,094,820 | 3/1992 | Maxwell et al. | 422/82.12 |
| 5,125,891 | 6/1992 | Hossain et al. | 604/34 |
| 5,152,746 | 10/1992 | Atkinson et al. | 604/31 |
| 5,176,629 | 1/1993 | Kullas et al. | 604/31 |
| 5,195,960 | 3/1993 | Hossain et al. | 604/34 |
| 5,267,956 | 12/1993 | Beuchat | 604/30 |
| 5,318,515 | 6/1994 | Wilk | 604/30 |
| 5,320,502 | 6/1994 | Davis | 417/474 |
| 5,344,292 | 9/1994 | Rabenau et al. | 417/413 |
| 5,399,160 | 3/1995 | Dunberger et al. | 604/31 |
| 5,403,277 | 4/1995 | Dodge et al. | 604/30 |
| 5,476,368 | 12/1995 | Rabenau et al. | 417/395 |

OTHER PUBLICATIONS

"Arthroflator", brochure of F.M. Wiest Kg, Munich, Germany, 4 pages, undated.

"Arthroscophistication", brochure of Orthopedice Products Division/3M, 2 pages (1986).

J. Gillquist, "Acute Knee Arthroscopy", *O'Connor's Textbook of Arthrosopic Surgery*, IES™ 1000 Integrated Endoscopy System, brochure of Arthrotek, 7 pages, undated.

"Integrating Innovative Fluid Management with Arthroscopic Cutting Excellence", brochure of Smith & Nephew Dyuonics, Inc., Andover, MA, 6 pages, undated.

"New 3M Arthroscopy Pump", brochure of Orthopedic Products Division/3M, 4 pages (1986).

"Operators Manual 3M Arthroscopy Pump", brochure of Orthopedic Products Division/3M, 15 pages (1986).

"Ortho–Arthropump", brochure of Orthoconcept S.A., Meyrin, Switzerland, 3 pages (Sep. 1986).

"Surgeon's Guide 3M Arthroscopy Pump", brochure of Orthopedic Products Division/3M, 15 pages, undated.

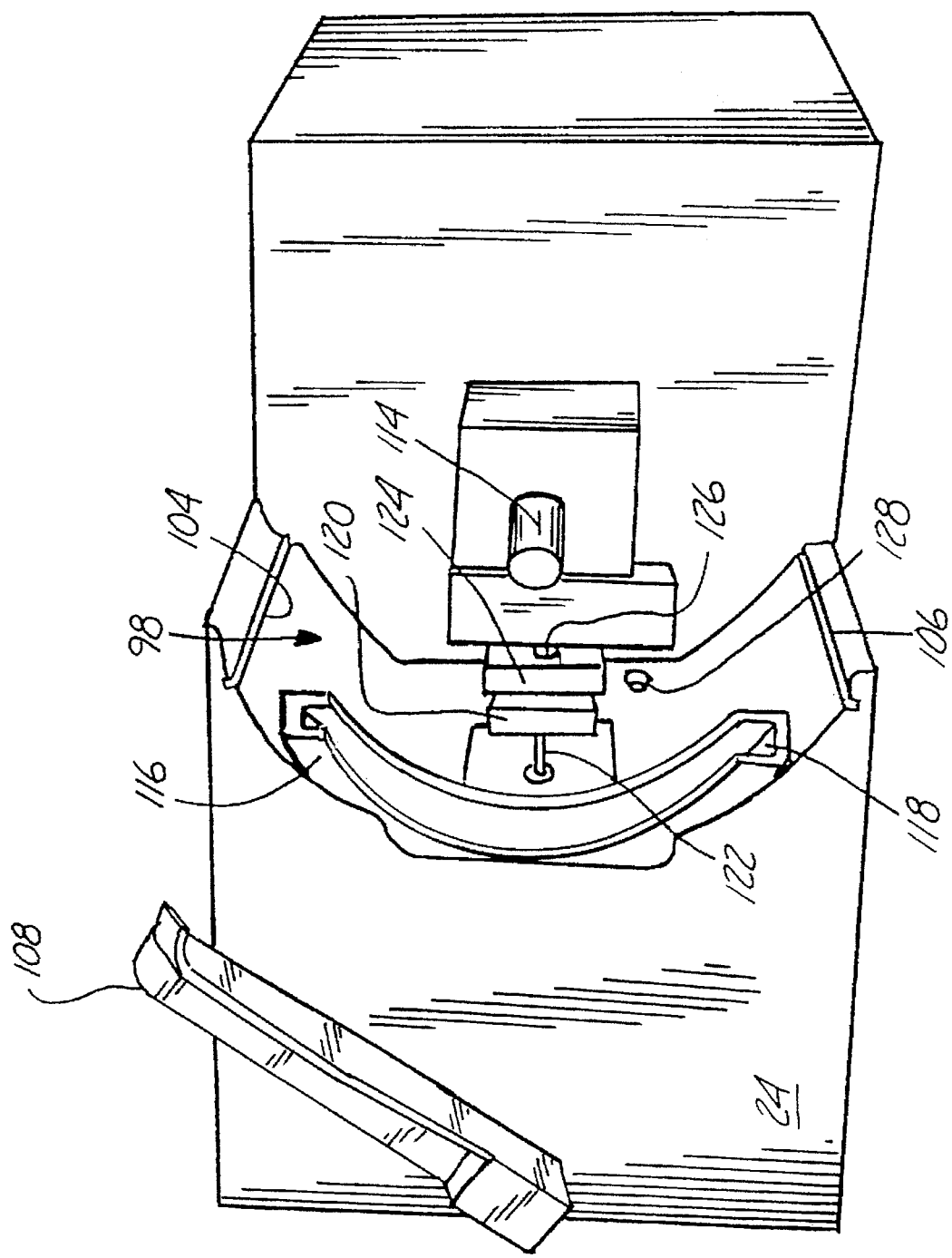

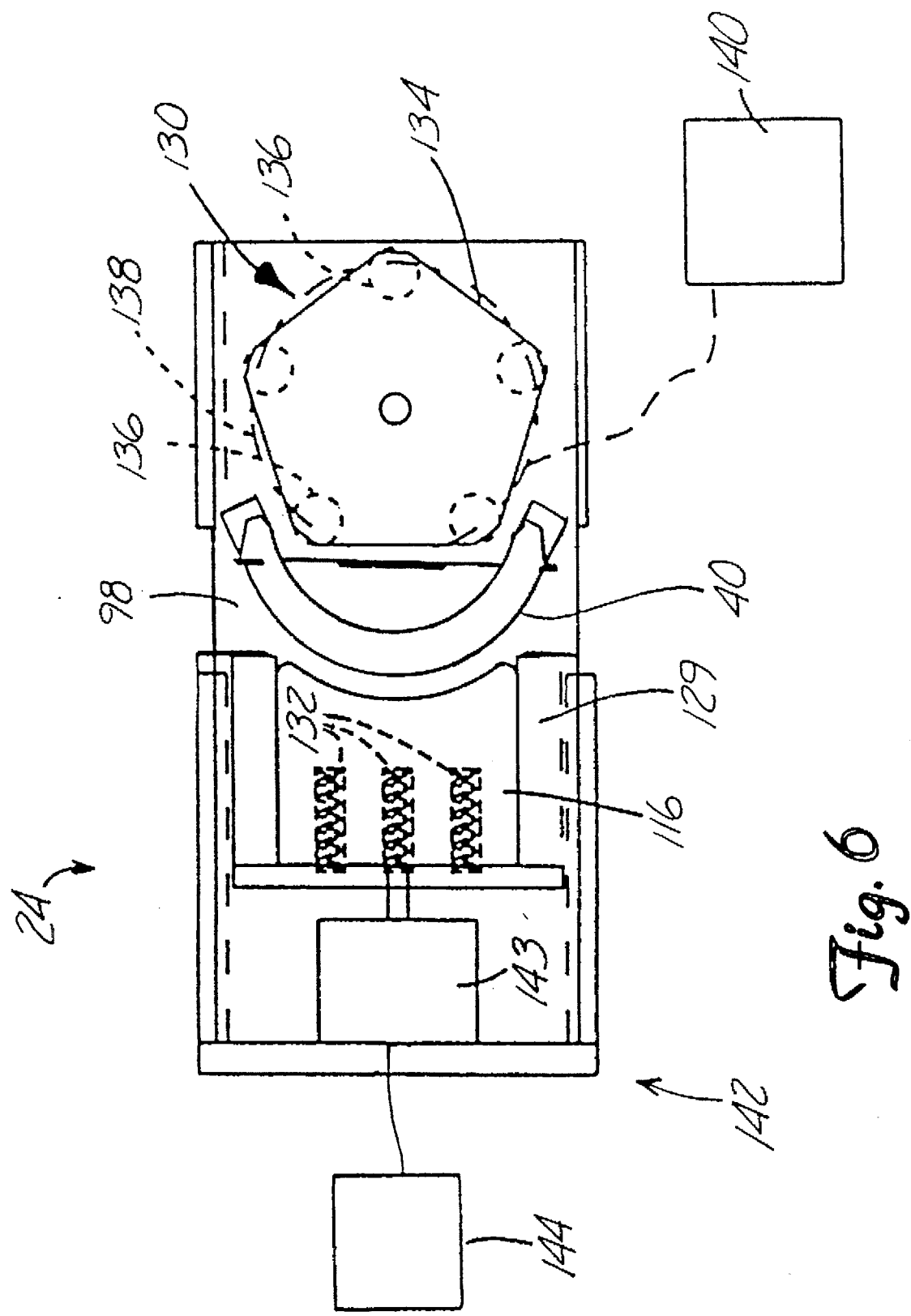

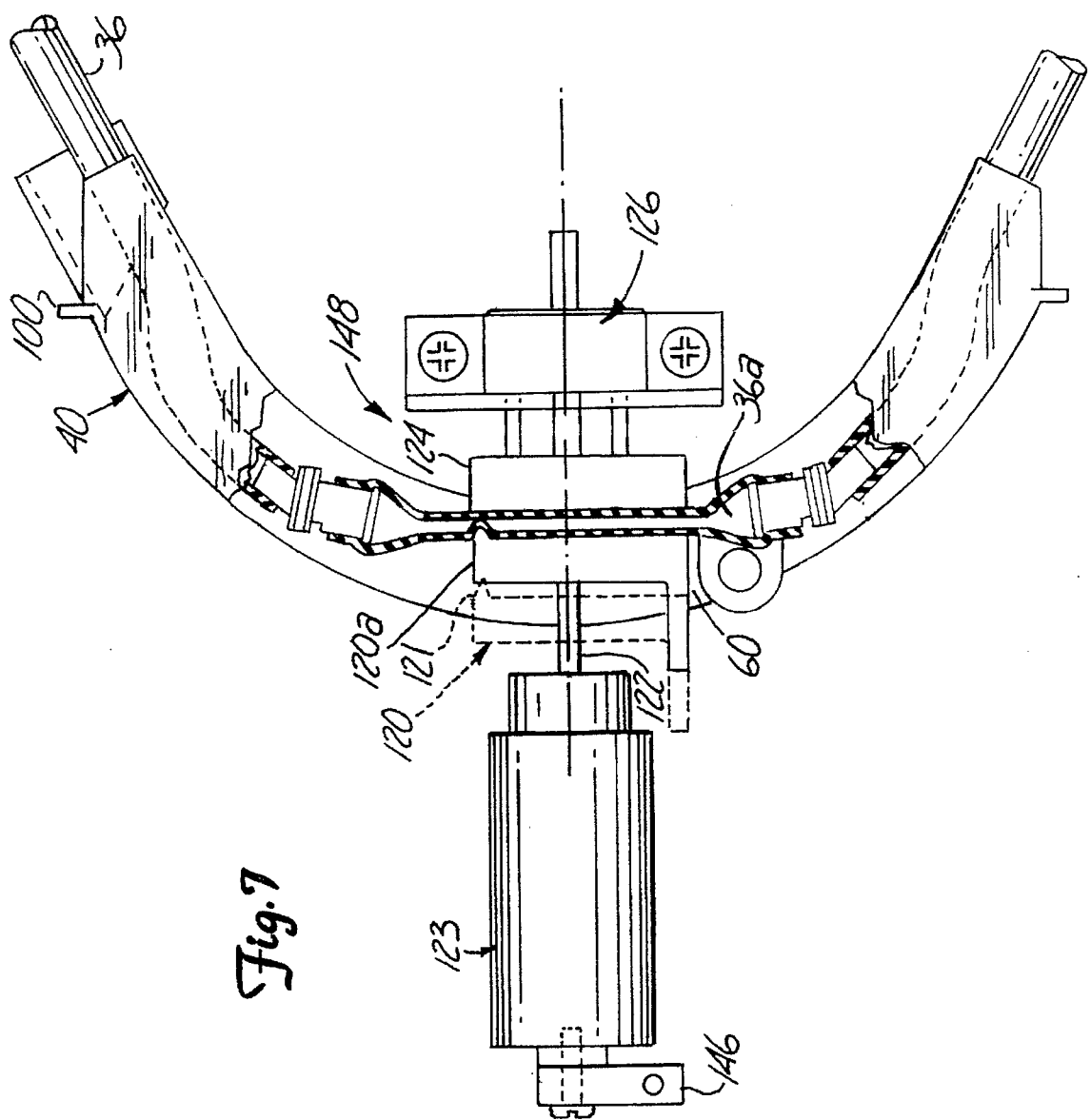

IRRIGATION SYSTEM WITH TUBING CASSETTE

RELATED U.S. APPLICATION DATA

This application continuation of PCT/US94/00563, filed Jan. 12, 1994, which is a continuation-in-part of Ser. No. 08/003,475, filed Jan. 12, 1993, now U.S. Pat. 5,403,277, which is hereby incorporated by reference.

FIELD OF THE INVENTION

The present invention relates to the field of irrigation systems used during endoscopic procedures. More particularly, the present invention relates to an irrigation system incorporating a tubing cassette to simplify setup and breakdown of the irrigation system between procedures.

BACKGROUND OF THE INVENTION

The use of irrigation systems including pumps is described in detail in commonly-assigned U.S. Pat. No. 4,650,462. Irrigation with a fluid, typically saline solution, is provided during endoscopic procedures such as arthroscopy to distend the joint, improve viewing of the area being treated, and to remove debris which may be loosened during the procedure.

Irrigation systems such as those described in U.S. Pat. No. 4,650,462 provide substantially independent control over both flow through the area being treated and pressure of the fluid in that area. Irrigation systems which do not provide independent control over pressure and flow typically suffer from either insufficient flow to present a clear treatment site or excessive pressure which can cause other serious problems.

Irrigation systems deliver and remove fluid to the treatment site using surgical tubing. Because of biological contamination, the tubing must be replaced between procedures. Considerations regarding tubing and tubing sets used in irrigation systems are thoroughly discussed in commonly-assigned U.S. Pat. No. 4,820,265. Briefly, the tubing set must include an inflow tube to provide irrigation fluid to the treatment site and an outflow tube to remove the irrigation fluid from the treatment site. Tubing sets used with irrigation systems which monitor fluid pressure at the treatment site (such as that described in U.S. Pat. No. 4,650,462) also typically include a pressure sensing line connected between the treatment site and the irrigation system.

The pumps and tubing sets disclosed in the references discussed above use a bifurcated tubing assembly in the outflow line. One pathway of the bifurcation incorporates an outflow control section of circular cross-section which interfaces with occlusion hardware in the pump to create a fully open or fully closed valve. The valve is powered by a solenoid which pinches the outflow control tubing section against a fixed back plate. The other pathway includes a thin-walled relief section of circular cross-section which interfaces with relief hardware in the pump. The relief section is pinched by a spring-loaded plate which is designed to open the valve partially at a pressure of about 50 mmHg and fully at a pressure of about 200 mmHg. When opened, fluid passes through the relief section to reduce pressure at the irrigation site.

This arrangement has been commercially successful, but the tubeset is time-consuming and relatively complicated to load in the pump, has a higher than desirable factory cost, and wastes irrigation fluid due to the low cracking pressure of the relief section.

An additional problem with many known irrigation fluid systems including pressure sensing lines is the use of couplings in those lines which introduce errors into the pressure reading. The primary cause of the error is the use of couplings which require axial compression to provide adequate sealing between fittings. Examples of such couplings include luer-type lock fittings and other quick disconnect type fittings.

SUMMARY OF THE INVENTION

The present invention provides a tubing set in cassette form and an irrigation system employing the cassette and tubing set for use in endoscopic procedures.

The tubing set according to the present invention includes a generally arcuate cassette which is inserted into the pump housing to effect a change in tubing sets between procedures. The use of a generally arcuate cassette provides many advantages over known methods and apparatus currently used to manage tubing in irrigation systems.

The preferred cassette incorporates both inflow and outflow lines as well as a pressure sensing line, thereby eliminating the need for operators to thread tubing through the pump or through any pressure control devices which may be present in the irrigation system. As a result, setup time is significantly reduced and the possibility of setup error in the threading of fluid lines through the irrigation pump/pressure control system is eliminated.

The preferred cassette also eliminates the use of expensive components such as pump heads and/or races in the cassette. The tubing in the preferred cassette is exposed within openings in the cassette, thereby allowing a peristaltic pump to operate on the tubing to pump irrigation fluid. Eliminating expensive components in the cassette design minimizes cost and waste when the cassettes are provided as disposable units to prevent contamination between procedures.

The preferred outflow line contained in the tubing set incorporates a flattened tubing segment including a pair of interior corners. In the preferred irrigation system, a combination occlusion/relief valve which acts on the segment within the preferred cassette to control irrigation fluid pressure at the irrigation site. The preferred tubing segment's cross-sectional profile facilitates pressure control, resists being completely closed, and re-opens easily after closure.

The irrigation system according to the present invention receives the arcuate cassette and tubing set according to the present invention. The preferred irrigation system provides substantially independent control over pressure and flow of the irrigation fluid. By employing the cassette and tubing set of the present invention, the irrigation system provides for convenient tubing setup and replacement before and between procedures.

The preferred irrigation system includes a valve assembly which compresses the outflow tubing segment to restrict outflow from the irrigation system, thereby controlling pressure at the irrigation site. The preferred valve assembly includes a control pad and relief pad, both of which may be mounted on solenoids to control pressure in the irrigation system.

The preferred control pad includes an anvil to assist in occluding the outflow tubing segment and a pressure pad, both of which are located opposite the relief pad. A control solenoid moves the control pad towards or away from the relief pad to compress the outflow tubing segment, thereby restricting fluid flow through the outflow line. The anvil reduces the amount of force required to occlude the outflow tubing segment while the pressure pad of the preferred control pad serves as one component of the pressure relief mechanism in the preferred system.

The solenoid on which the control pad is mounted provides a predetermined maximum force. That predetermined maximum force limits the maximum pressure developed at the irrigation site because excess fluid pressure within the outflow tubing segment will move the control pad away from the relief pad, thereby moving the anvil away from the relief pad to increase fluid flow through the outflow tubing. By increasing flow within the outflow line, the irrigation fluid pressure at the irrigation site can be lowered.

The relief pad is also preferably mounted on a solenoid which also provides a predetermined maximum force. The relief pad is stationary during operation and provides a predictable backstopping force against which the control pad operates to compress the outflow tubing segment. Conversely, the control pad operates as a backstopping force against which the relief pad operates.

By mounting the relief pad on a solenoid or on any other mechanism which provides a predetermined maximum force, the relief pad also functions as a component of the pressure relief mechanism in the preferred irrigation system. If pressure within the outflow line exceeds a predetermined level (corresponding to the force provided by the relief solenoid), the relief pad will move away from the outflow tubing segment, thereby increasing outflow from the irrigation site through the outflow tubing and, consequently, reducing pressure at the irrigation site.

The preferred irrigation system also includes a pressure sensing line for monitoring irrigation fluid pressure at the irrigation site. This pressure sensing line interfaces with a port on the pump housing for communicating information to the pump controller. The pressure line ends in a fitting which floats to compensate for alignment errors between the cassette and the pump, and which minimizes pressure monitoring inaccuracy by sealing with a fixed port on the pump housing using a coupling which does not require axial compression to seal. The preferred coupling incorporates a face seal between the fitting and port.

The irrigation system according to the present invention also includes a peristaltic pump which moves irrigation fluid through the tubing set by deforming the inflow tubing against a race. The preferred pump incorporates a rotating pump head including a plurality of rollers, with each roller deforming the tubing and moving along a portion of its length proximate the race to move fluid through the tubing and to the treatment site.

The irrigation system according to the present invention also includes means for moving the race and pump head relative to each other to simplify cassette insertion and removal. In the preferred embodiment, cassette insertion and removal is accomplished with a simple linear movement of the cassette into a passageway in the pump housing.

These and various other features and advantages of the present invention will become apparent upon reading and review of the following detailed description, accompanying drawings and claims.

BRIEF DESCRIPTION OF THE DRAWINGS

FIG. 5 is a front quarter perspective view of the fluid control module, wherein a cover is removed to show interior details.

FIG. 6 is a cut-away side view of the fluid control module.

FIG. 7 is a side section detail view of the valve means which provides outlet control.

DETAILED DESCRIPTION OF PREFERRED EMBODIMENTS

Figure 1:
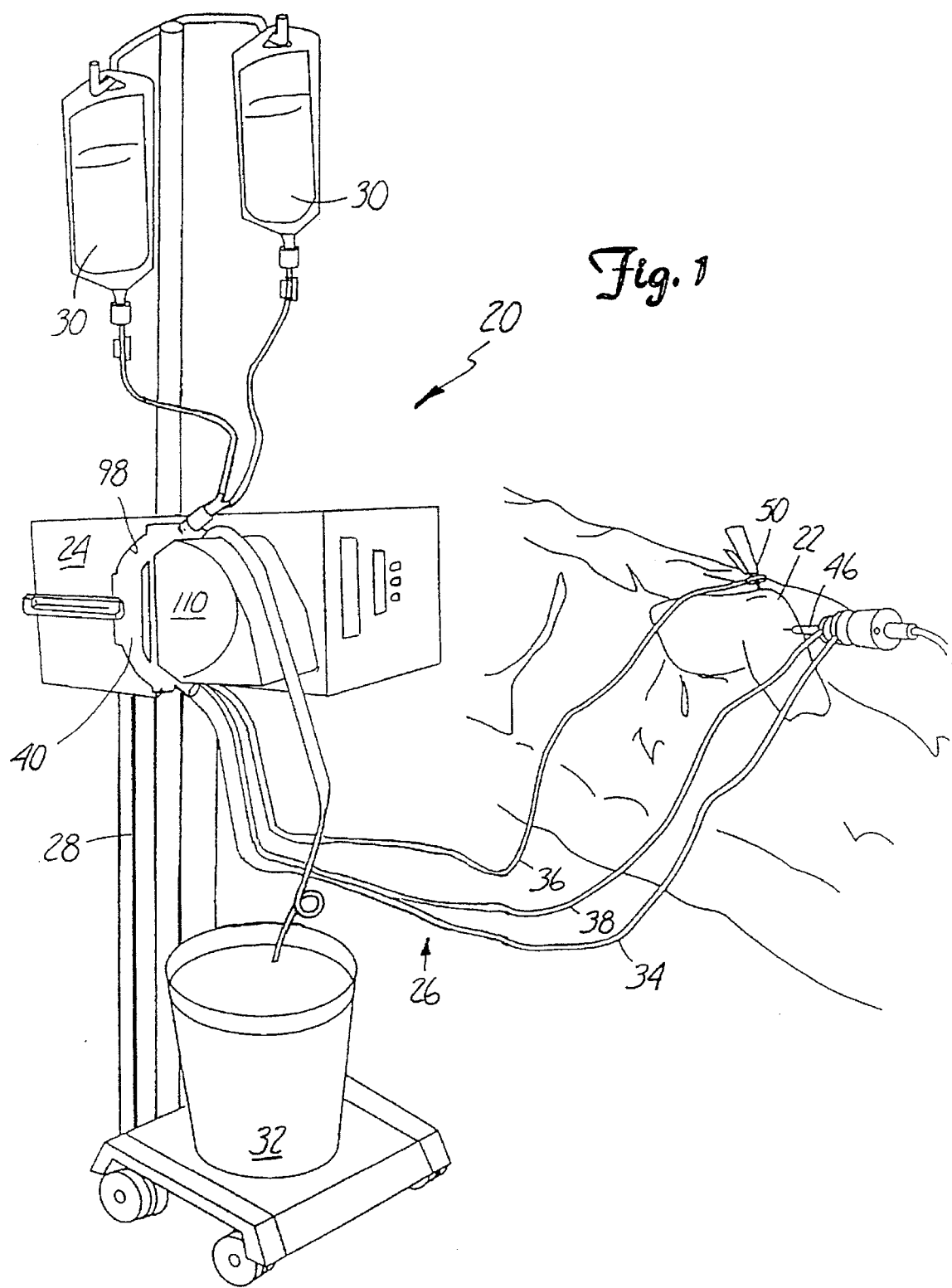
FIG. 1 is a perspective view of one preferred embodiment of the irrigation system of the present invention.

Now referring to FIG. 1, one embodiment of an irrigation system according to the invention is designated in its entirety by the reference numeral 20. The irrigation system 20 is particularly adapted for use in endoscopic procedures for maintaining and controlling flow of irrigation fluid to an internal body irrigation site. As specifically depicted in FIG. 1, the irrigation system 20 may provide irrigation fluid to the knee 22 during arthroscopic surgery. Commonly-assigned U.S. Pat. Nos. 4,650,462 and 4,820,265 and commonly-assigned U.S. patent application Ser. No. 08/233,309 filed Apr. 26, 1994 titled IRRIGATION TUBING SET HAVING COMPLIANT SECTIONS, relate to various aspects of this type of irrigation system, and are incorporated herein by reference.

Irrigation System Components

As illustrated in FIG. 1, the irrigation system 20 generally comprises a fluid control module or irrigation pump generally designated 24 and a tubing set generally designated 26. As used herein, "fluid control module" means a module for controlling fluid flow and/or pressure, for example, by means of a valve mechanism and/or a fluid pump, and is not limited to an irrigation pump. A stand 28 may be provided for supporting the fluid control module 24, along with one or more irrigation fluid reservoirs 30 and a fluid collection reservoir, such as a bucket 32. Other collection mechanisms may be used with the present invention as well.

In one aspect of the invention, the tubing set 26 preferably includes inflow, outflow and pressure sensing lines 34, 36 and 38, respectively, and a cassette 40 facilitating the interface of the tubing set 26 with the fluid control module 24. In the preferred embodiment, the cassette 40 is manually inserted into and removed from a cassette receiving passageway 98 in the fluid control module 24.

The upstream portion of the inflow line 34 is in fluid communication with the irrigation fluid reservoirs 30 by any suitable conventional means, such as a bag spike 68, and the downstream portion of the inflow line 34 is in fluid communication with an inflow cannula 46 to provide irrigation fluid to the irrigation site 22.

The upstream portion of the outflow line 36 is connected in fluid communication with a conventional outflow cannula 50 to drain irrigation fluid from the irrigation site 22, and the downstream portion of the outflow line 36 drains the irrigation fluid into the bucket 32. The outflow line 36 may optionally have a loop 72 (commonly referred to as a "pig tail") to maintain fluid in the outflow line 36 when pumping is halted (see FIG. 2). The irrigation fluid reservoirs 30 are preferably positioned above the fluid control module 24, and the fluid collection bucket 32 is preferably positioned below the fluid control module 24.

The inflow cannula 46 may be a pressure-sensing scope inflow cannula 46 of the type described in commonly-assigned U.S. Pat. No. 5,037,386, which is incorporated herein by reference. It will, however, be understood that other devices and cannulas could be substituted or used with the irrigation system 20 of the present invention. The pressure sensing function could also alternately be performed at the outflow cannula 50 as opposed to the inflow cannula 46 or at a separate cannula (not shown) dedicated to the pressure sensing function.

The preferred pressure sensing line 38 comprises pressure-sensing tubing 38 in fluid communication with a pressure-sensing port on the inflow cannula 46 to provide a fluid column (e.g., air) between the irrigation site 22 and the fluid control module 24. One embodiment of a preferred pressure sensing tubing 38 and method of monitoring pressure using the same is described in commonly-assigned U.S. Pat. No. 4,820,265, which is incorporated herein by reference.

Tubing Set

Figure 2:
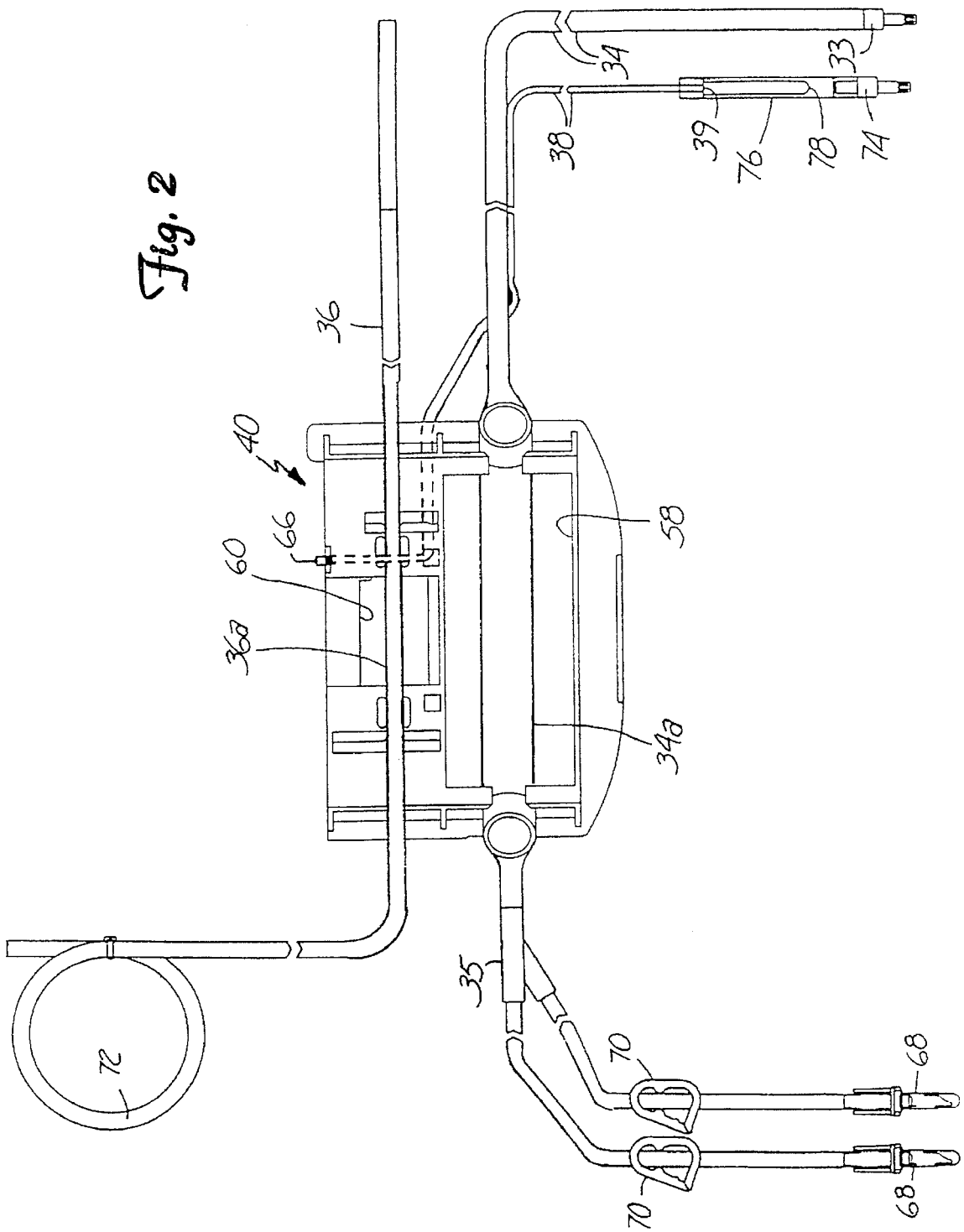
FIG. 2 is a plan view of one preferred embodiment of the tubing set and cassette according to the present invention.

FIG. 2 illustrates a preferred embodiment of the tubing set 26 of the invention, in which the tubing set 26 comprises inflow, outflow and pressure sensing lines 34, 36 and 38, and a cassette 40 encasing portions of the inflow and outflow lines 34 and 36 between their upstream and downstream ends and holding an end of the pressure sensing line 38 for connection with the fluid control module 24.

Figure 9:
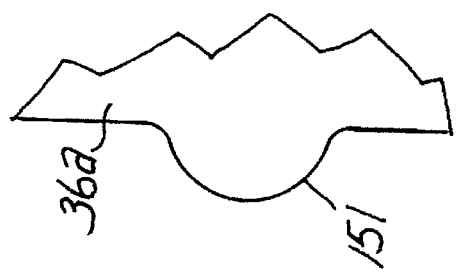
FIG. 9 is a detail view of a portion of the cross-section depicted in FIG. 8A.

The preferred cassette 40 includes an opening 58 exposing opposite sides of segment 34a of the inflow line 34 for engagement by a pumping mechanism in the fluid control module 24, and a second opening 60 exposing segment 36a of the outflow line 36 for engagement by a valve mechanism of the fluid control module 24. The preferred segment 36a is a flattened portion of tubing which is connected to standard round tubing at each end by a fitting. The preferred segment 36a and associated fittings are depicted in greater detail in FIGS. 7–9 and described in detail below. Although the preferred segment 36a is flattened, it will be understood that standard round tubing could be provided for operation on by the valve assembly of the preferred fluid control module 24.

Figure 10:
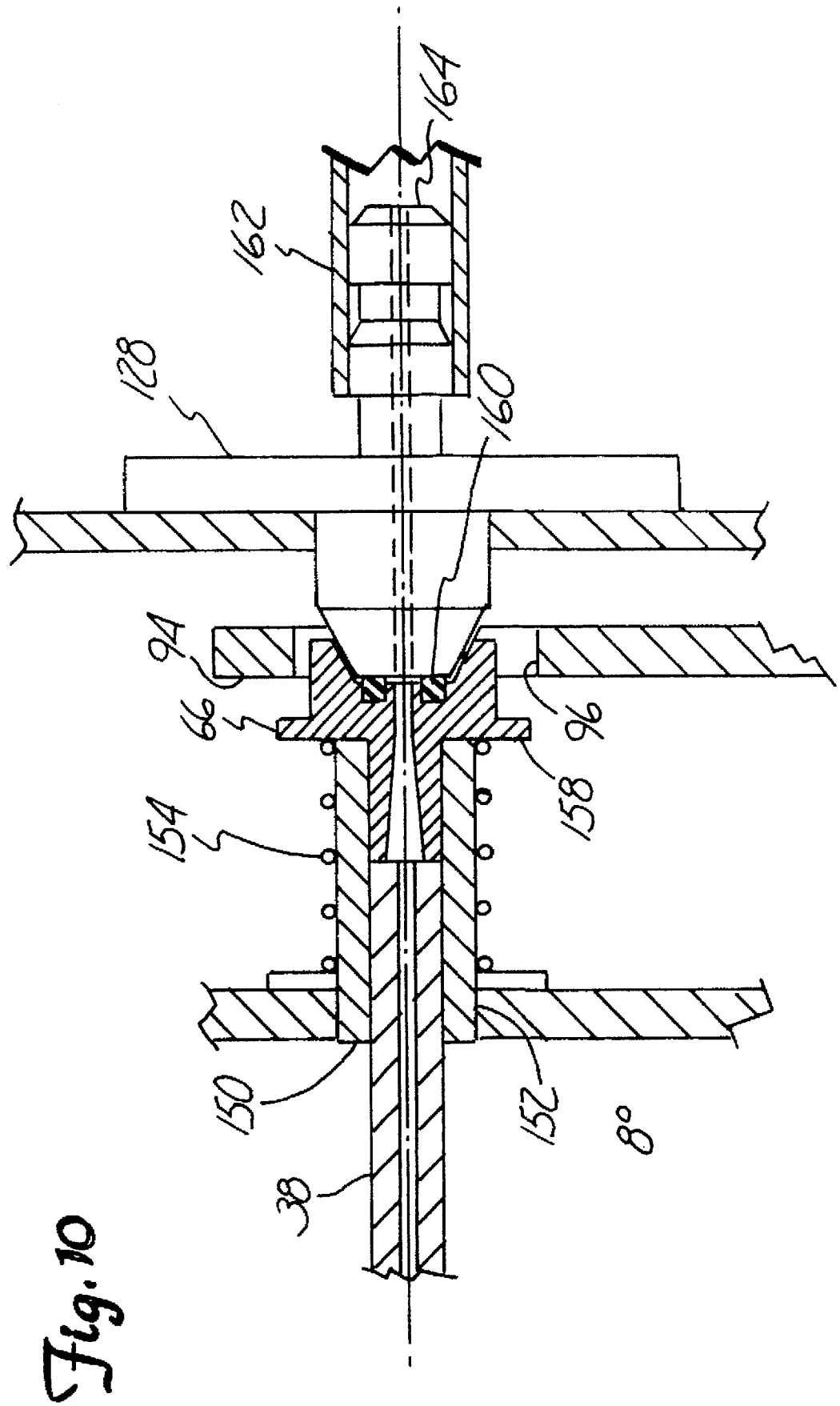
FIG. 10 is a detail cross section view of the interaction between the pressure sensing line fitting and the pressure port in the fluid control module.

The preferred cassette 40 depicted in FIG. 2 also includes a fitting 66 in communication with the pressure sensing line 38 to complete its connection to the fluid control module 24. The preferred fitting 66 is depicted in FIG. 10 and described in greater detail below.

The upstream portion of the inflow line 34 preferably includes a Y-fitting 35, and also includes any suitable means for connection to the irrigation fluid reservoirs 30, such as conventional bag spikes 68. Conventional pinch clamps 70 may be provided on the branched segments of the upstream portion of the inflow line 34 to allow either one of the branched segments to be closed off, for example, to permit replacing one of the reservoirs 30 without stopping the fluid control module 24. Closing the pinch clamp 70 on one branch maintains prime in that branch even when the respective reservoir 30 is removed. The downstream end of the inflow line 34 is provided with any suitable connector 33 for connection to the inflow cannula 46.

The downstream portion of the outflow line 36 may be provided with a loop 72 ("pig tail") to provide a fluid trap to prevent a loss of irrigation fluid in the downstream portion of the outflow line 36 when fluid flow is halted.

The free end 39 of the pressure sensing line 38 is provided with any suitable connector to connect the line 38 to the pressure sensing cannula 46, including for example, a male luer-type lock 74 to connect the free end of the pressure sensing line 38 in fluid communication with a female luer-type lock at the pressure sensing port of the pressure sensing inflow cannula 46.

As described in U.S. Pat. No. 4,820,265, the pressure-sensing line 38 preferably includes diaphragm-containing chamber 76 containing a pressure transmitting diaphragm 78, such that the irrigation fluid is kept out of the pressure sensing line 38 between the diaphragm 78 and the fluid control module 24 so that the pressure-sensing line 38 forms a gas column (e.g., air). The gas column in pressure-sensing line 38 preferably routes through the cassette 40 and terminates in a fitting 66.

Cassette

Figure 3:
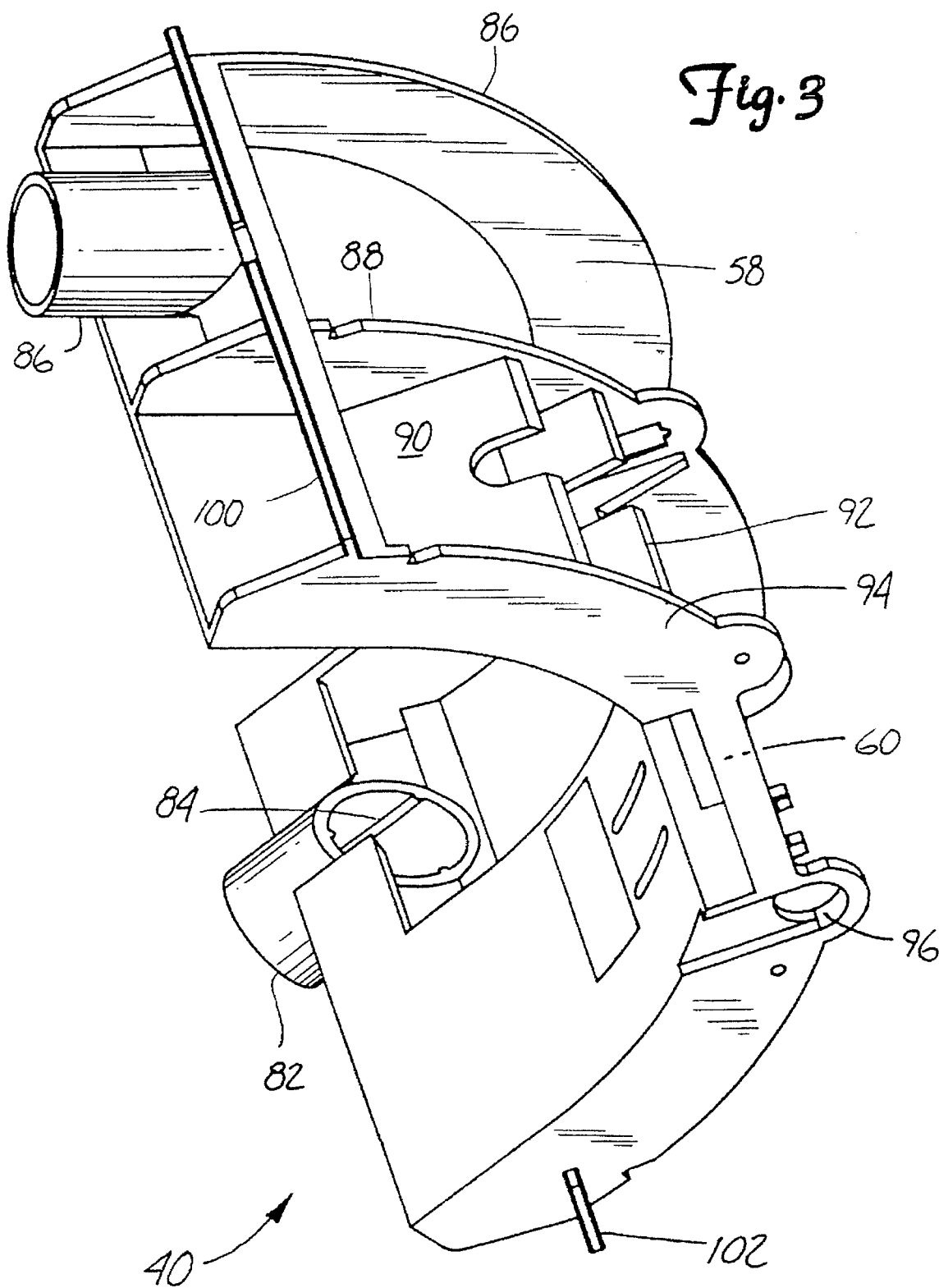
FIG. 3 is a perspective view of the cassette according to the present invention.
Figure 4:
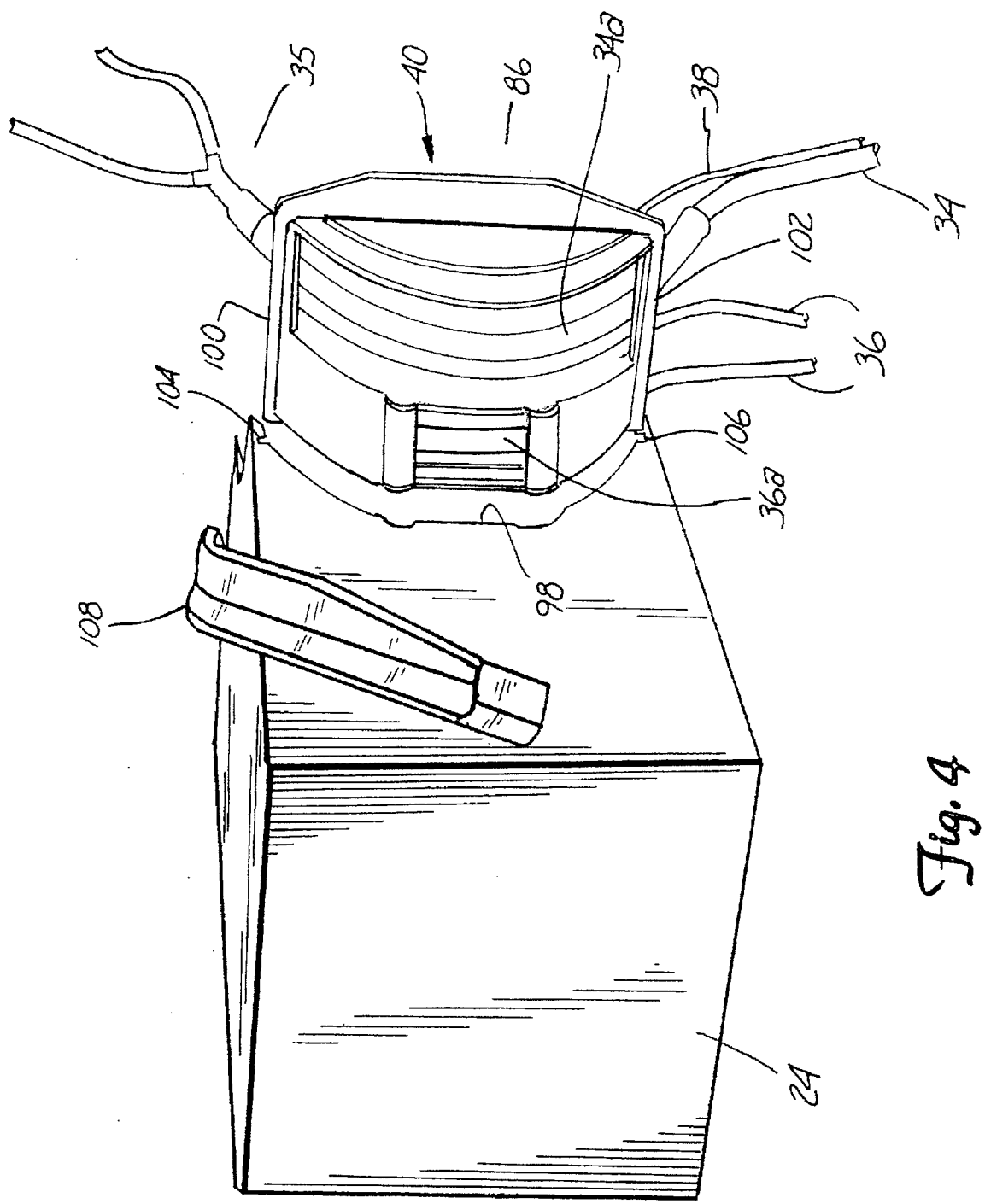
FIG. 4 is a rear quarter perspective view of the fluid control module.

A preferred cassette 40 is depicted in FIGS. 2–4. As shown best in FIGS. 3 and 4, the cassette 40 has a generally arcuate shape. This shape could alternately be described as C-shaped or, in geometric terms, as an arcuate section of a cylinder taken along its longitudinal axis. In the geometric definition, it will be understood that the cylinder is not limited to a circular cross-section. This general shape assists in design of the preferred fluid control module 24 as well as cassette 40 because it generally conforms to the shape of the pump head 130 to which rollers 136 are attached (see FIG. 6A). As a result, the amount of material needed to form cassette 40 is reduced. Furthermore, the arcuate shape provides an inherent alignment means to assist the user in aligning the cassette 40 for insertion into fluid module 24.

Turning to FIG. 3, where one preferred embodiment of a cassette 40 is depicted in perspective view without tubing, it can be seen that provision is made for holding the inflow line 34 at two places via sleeves 80 and 82. Sleeve 82 includes internal ribs 84 to facilitate gripping the inflow line 34. Side wall 86 and interior wall 88 define the margins of opening 58, through which segment 34a of inflow line 34 can be acted on by the irrigation pump 24.

Similarly, provision is made for aligning and holding the outflow line 36 and its tubing segment 36a via notched partitions 90 and 92 and similar ones hidden from view on the opposing side of the cassette 40. Side wall 94 and interior wall 88 define the margins of opening 60, through which segment 36a of inflow line 34 can be acted on by the fluid control module 24. In the preferred embodiment, notch 92 (closest to the opening 60), cooperates with slots 172 formed in fittings 170 used to connect flattened tubing segment 36a with the remainder of outflow tubing line 36 (see FIG. 8B). That cooperation between notches 92 and slots 172 in fittings 170, maintains the proper positioning of tubing segment 36a within opening 60.

Also in the preferred cassette 40, pressure sensing line 38 is routed through the cassette 40 to a fitting 66. A hole 96 is provided in exterior wall 94 to facilitate the placement of the fitting 66, as will be shown in greater detail in FIG. 10.

In addition to the arcuate shape of the cassette 40, an additional alignment mechanism is also provided in the preferred cassette 40 to ensure that it is located in the proper position within cassette-receiving passageway 98 before pumping is begun, as well as to help retain the cassette 40 in the proper position during operation. As part of the preferred alignment mechanism, a pair of alignment ribs 100 and 102 are located on the upper and lower margins of the cassette 40. As will be better appreciated in connection with FIG. 4, the alignment ribs 100 and 102 fit into complementary slots 104 and 106 adjacent the cassette-receiving passageway 98 of fluid control module 24. It will be understood that many other mechanisms for providing control over the position of the cassette could be substituted for the preferred mechanism described herein.

The preferred cassette 40 can be manufactured using many different materials and processes. Some preferred materials include, but are not limited to: polyethylene, polypropylene, ABS, high impact styrene and polycarbonate. The cassette 40 can also be manufactured by many known methods, particularly injection molding.

Also contemplated for use in the cassette 40 of the present invention is the use of an identification system which would automatically indicate the origin or intended use (for various procedures) for the cassette 40 upon insertion into a fluid control module 24. For example, the identification system could indicate whether the tubing set is intended for use in a large joint (e.g., the knee) or a small joint (e.g., the wrist). Such identification systems could include a bar code or electrical binary code on the cassette 40 and associated bar code or other reader mounted in the fluid control module 24, an IC chip embedded into the cassette 40 which is interrogated by corresponding circuitry in the fluid control module 24, or a mechanical identification system which could incorporate, for example, a void formed in the cassette which may or may not cooperate with an optical source and sensor or mechanical limit switch. It will be understood that many specific identification means could be used to accomplish the intended result as described above.

Fluid Control Module

The preferred fluid control module 24 depicted in the drawings includes a cassette-receiving passageway 98 for releasably receiving the cassette 40 of tubing set 26. Once in position, a peristaltic pump operates on the inflow tubing segment 34a in cassette 40 to pump irrigation fluid through the irrigation site 22. A valve assembly in the fluid control module 24 operates on the outflow tubing segment 36a in cassette 40 to control fluid pressure at the irrigation site 22.

The present invention contemplates the use of a peristaltic pump to operate on segment 34a of the inflow line 34. Peristaltic pumps are preferred as they do not include any parts which contact the irrigation fluid during normal operation. As a result, contamination and cleaning are not critical issues which must be addressed by users of the fluid control module. Although the preferred peristaltic pump is a rotary version, it will be understood that any pump mechanism which uses peristaltic pumping principles could be substituted into the fluid control module 24 in place of the preferred rotary peristaltic pump.

FIG. 4 depicts a rear quarter perspective view of a preferred fluid control module 24. Cassette-receiving passageway 98 preferably opens on the side panel of the fluid control module 24, and, in this view, the cassette 40 is depicted as about to be inserted into the passageway 98. It can be seen that the passageway 98 includes a pair of slots 104 and 106 which are sized to receive the alignment ribs 100 and 102 located on the top and bottom of the cassette 40. The ribs 100 and 102 and slots 104 and 106 cooperate to ensure that the cassette 40 is placed in passageway 98 with the correct orientation.

Also depicted in FIG. 4 is a lever 108. As will be described in more detail below, after the cassette 40 has been inserted into the passageway 98, the lever 108 is rotated into a horizontal position to physically block the cassette 40 in the passageway 98 and move a race 116 (seen in FIG. 5) toward the cassette 40 and against the segment 34a of the inflow tubing 34 for pumping.

Referring now to FIG. 5, a front quarter perspective view of the fluid controller 24 of FIG. 4 is illustrated. A cover 110 which, as seen in FIG. 1, shields the forward side of the passageway 98, has been removed for clarity. Pump head 130, which is normally mounted on shaft 114, has also been removed for clarity. The race 116 has a curved interior surface 118 which contacts the held portion 34a of inflow tubing 34 when the cassette 40 is installed and the lever 108 moved into its horizontal position.

When the lever 108 is rotated to its horizontal position, control pad 120 is moved as the lever 108 moves a carriage 146 connected to one end of plunger 122 on which the control pad 120 is mounted. Such movement places control pad 120 in close proximity to segment 36a of outflow tubing 36 by moving the control pad 120 towards the relief pad 124 which is also, in preferred embodiments, mounted on the plunger of a solenoid 126.

One advantage of this arrangement is that movement of lever 108 and the corresponding movement of the carriage 146 places plunger 122 in its optimum operating range with respect to fixed solenoid 123. It also allows the control pad 120 to be withdrawn farther than possible if only solenoid 123 were used to withdraw the control pad 120 from the tubing segment 36a (because of its relatively limited operating range in the preferred embodiment).

A port 128 is also preferably provided within the passageway 98, adapted to mate with fitting 66 on preferred cassette 40 to convey information about the pressure at the irrigation site 22 to the fluid control module 24. More details regarding connection of the pressure sensing line 38 to the port 128 are provided below in connection with FIG. 10.

Referring now to FIG. 6, a cutaway side view of the preferred fluid control module 24 is shown. A race 116 is mounted on one side of the cassette-receiving passageway 98, and a pump head 130 is mounted on the other side of the cassette-receiving passageway 98, opposite the race 116. The arrangement is such that the race 116 engages segment 34a of the inflow line 34 through opening 58 in the cassette 40 when the cassette 40 is located in the cassette-receiving passageway 98.

In the preferred embodiment, the race 116 is mounted on a support 129 which permits longitudinal motion forward towards the pump head 130, or rearward to permit the cassette 40 to be removed.

Although five rollers 136 are depicted in the figures, it will be understood that any lesser or greater number of rollers 136 could be used within the scope of the present invention.

In use, pump head 130 rotates about its center point to deform segment 34a of inflow line 34 against the race 116 to pump irrigation fluid through the inflow line 34. The rotation of pump head 130 is supplied by motor 138 located directly behind the side bulkhead of the housing adjacent the cassette-receiving passageway 98 near the pump head 130 in the preferred embodiment depicted in FIG. 6. It will be understood that the motor 138 could also be placed in other locations and a drive train provided, if desired.

Motor 138 is preferably controlled by motor controller 140 which controls both the rotational speed of the pump head 130, thus controlling flow and/or pressure of the irrigation fluid. In addition, control over the stationary position of pump head 130 could be helpful in some systems. For example, when the pump head 130 is stopped during a procedure, at least one of the rollers 136 could be maintained in contact with the exposed segment 34a of inflow line 34 to prevent the irrigation fluid from reversing its direction of flow. Although a DC motor 138 and suitable controller 140 are preferred, it is contemplated that many different types and combinations of motors and motor controllers could be used in conjunction with the present invention.

Because the preferred pump 24 is a rotary peristaltic pump, fluid flow through the system is generally pulsed because of the action of each individual roller 136 on the inflow tubing segment 34a. In some instances, however, the user may want to minimize the pulsing action while in other instances the pulsing action is preferably maximized. The rotation of pump head 130 can be controlled to impart certain pulsing characteristics. That method of control is, however, limited by the fluid flow requirements of the system 20 as well as other considerations. A discussion of means by which the pulsing characteristics can be conveniently controlled in a rotary peristaltic pump is provided in U.S. Ser. No. 08/003,475.

The preferred irrigation pump 24 also includes means for moving the race 116 and the pump head 130 relative to one another between a release position and an operating position. In the release position, the race 116 and pump head 130 are sufficiently spaced apart to allow the cassette 40 to be inserted into and removed from the cassette-receiving passageway 98. In the operating position, the race 116 and pump head 130 are positioned relative to one another such that the race 116 and pump head 130 engage segment 34a of inflow line 34 through the opening 58 in cassette 40 to deform segment 34a of inflow line 34 between the pump head 130 and race 116 to pump irrigation fluid to the irrigation site 22.

In the preferred embodiment, the means 142 for moving the race 116 and the pump head 130 relative to one another moves the race 116 relative to the pump head 130 between the release and operating positions. For example, the means for moving the race 116 may comprise a solenoid 143 mounted between the housing 24 and the race 116. If a solenoid is used, the solenoid may also be controlled by controller 144 which prohibits activation unless a signal is present from a sensor indicating that a cassette 40 is present in cassette-receiving passageway 98.

In the preferred embodiments, race 116 is resiliently mounted for movement towards and away from the center of rotation of pump head 130. Resilient mounting of race 116 provides a number of advantages. It can compensate for variations in the thickness of tubing operated on by the pump head 130 and also operates as a mechanical pressure relief mechanism on the inflow line 34 if that line were to become blocked at the cannula 46 or in the inflow line 34 leading up to the cannula 46. As depicted in FIG. 6, one or more compression springs 132 can be positioned to provide a resilient engagement of race 116 with the opposing pump head 130.

Figure 6A:
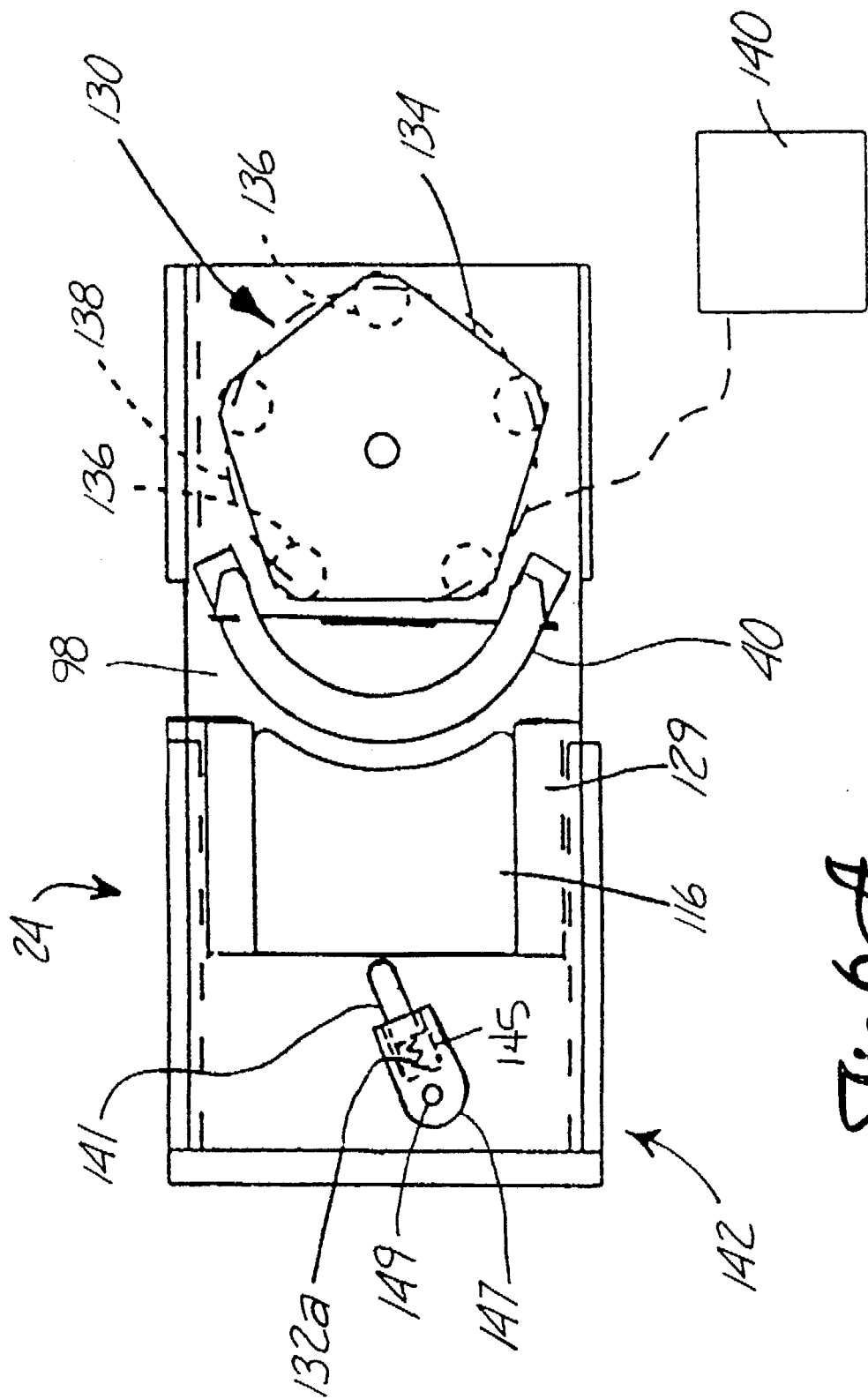
FIG. 6A is a view similar to that of FIG. 6 showing an alternate embodiment.

In FIG. 6A, an alternate means of moving the race is depicted. Here, the means for moving includes a push rod 141 which slidingly engages the rear part of the race 116 as it is moved within a bore 145 in a crank 147 which is turned by a shaft 149 coaxial with and rotating with lever 108. The push rod 141 is biased by one or more compression springs 132a within bore 145 to provide the benefits of resilient mounting of the race 116 discussed above.

It will be understood that many other means of moving the race 116 and pump head 130 relative each other could be provided in place of those specifically described with respect to the preferred embodiments above. Examples, include, but are not limited to: a cam system transferring rotational motion into longitudinal motion; and a screw drive or rack and pinion moving a base on which race 116 is resiliently mounted. It will also be understood that the race could be mounted stationary and/or fixed and that the pump head 130 could be moved into position and/or be resiliently mounted.

During operation of the pump, cassette 40 retains segment 34a of the inflow line 34 in alignment with the race 116 and pump head 130 but does not otherwise resist the forces applied by the race 116 and pump head 130. This arrangement is preferred because it reduces the strength and material requirements of the cassette 40 compared to cassettes (not shown) of the type including integral races or pumping mechanisms. As a result, the cost of the cassette 40 is typically lower than cassettes which include those additional components. This feature is particularly desirable if the tubing set 26 and cassette 40 are disposable. In addition to the economic advantages, the volume of waste produced when the cassette 40 is disposable is less with preferred cassette 40 than with cassettes having integral races and/or pumping mechanisms, thus providing an environmental advantage as well.

Occlusion/Pressure Relief Valve Assembly

Referring now to FIG. 7, a side view of the preferred valve assembly which controls fluid flow in the outflow line 36 is depicted. Segment 36a of outflow line 36 is seen as it extends through opening 60 of the cassette 40 where it can be acted on and compressed by the control pad 120 and the relief pad 124 to regulate the outflow of irrigation fluid from the irrigation site 22 (see FIG. 1), and thus regulate the pressure at the site.

The valve assembly preferably includes a control pad 120 located on one side of segment 36a and a relief pad 124 located on the other side of segment 36a, opposite the control pad 120. Control pad 120 is operatively connected to a control solenoid 123 via its plunger 122 which moves the control pad 120.

Control pad 120, in the preferred embodiment, includes two components for proper operation of valve assembly. An anvil 121 is located on the downstream end of the control pad 120 as shown. In the preferred embodiment, anvil 121 has an edge with a radius of approximately 1/32" (0.8 mm). Preferably, the anvil 121 extends across the face of the control pad 120. The anvil 121 improves control over fluid flow through outflow tubing segment 36a by reducing the amount of force required to occlude the segment 36a, thereby restricting flow which, in turn controls pressure at the irrigation site 22.

The remainder of control pad 120 also serves a purpose in the preferred embodiment. That area, which will be referred to as the pressure pad 119, provides feedback of the fluid pressure within the segment 36a to the solenoid 123 (through plunger 122). Fluid pressure in segment 36a provides a force against which solenoid 123 is operating. If that force exceeds the maximum force solenoid 123 can provide or is programmed to provide, then the control 120 and anvil 121 will be forced away from segment 36a, thereby relieving the flow restriction, and thus reducing fluid pressure at the irrigation site 22.

For proper operation of the valve assembly, anvil 121 must be located downstream from at least a portion of pressure pad 119. In one alternate embodiment, the anvil 121 could be located in the center of a pressure pad 119 (or at least located between two pressure pads which are not necessarily the same size). In that arrangement, flow through the valve assembly could be in either direction as the anvil 121 would always be located downstream from a pressure pad 119.

Although in the preferred embodiment, the pressure pad area 119 is operatively connected to the anvil 121 and solenoid 123 (through plunger 122), it will be understood that the pressure pad 119 could be provided as a separate pad not operatively connected to anvil 121. In that configuration, the pressure pad 119 could be mounted in a fixed position or it could be resiliently mounted for pressure relief if provided as biased against the segment 36a. If mounted for pressure relief, pressure pad 119 could, when forced away from its normal operating position, provide a signal which retracted the anvil 121 or performed another function, such as reducing motor speed, which acted to reduce fluid pressure in the segment 36a as well as at the irrigation site 22.

In the preferred valve assembly, relief pad 124 is also mounted for relieving pressure in the outflow tubing segment 36a. In the most preferred embodiment, the relief pad 124 is mounted on the plunger of a relief solenoid 126. Mounting relief pad 126 on a relief solenoid 126 accomplishes two purposes. First, it allows relief pad 124 to be retracted, if desired, to facilitate insertion and removal of cassettes 40 into passageway 98. Second, it allows the relief pad 124 to be held in position against the segment 36a with a predetermined maximum force. If the fluid pressure within segment 36a exerts a force greater than the predetermined maximum force provided by the relief solenoid 126, then fluid flow through segment 36a increases and, correspondingly, pressure at the irrigation site decreases.

Although relief pad 124 is preferably mounted on a relief solenoid 126, it will be understood that it could be mounted in any manner which allowed it to move in response to predetermined maximum allowable pressure within segment 36a. Alternatives could include, but are not limited to mechanical systems such as torsion or compression springs, etc.

Both solenoids 123 and 126 are preferably powered using constant current sources to minimize force variations due to changes in temperature due to power dissipation during operation. Control solenoid 123 can be either proportional or it can provide only on/off control over the movement of plunger 122 (and control pad 120). In the preferred system, control solenoid 123 is powered to provide a maximum fluid pressure of about 150 mmHg, while relief solenoid 126 is powered to provide a maximum fluid pressure of about 200 mmHg. As a result, if fluid pressure within tubing segment 36a exceeds about 150 mmHg, control pad 120 and anvil 121 are forced away from segment 36a, increasing fluid flow and decreasing pressure at the irrigation site 22. Relief pad 124 is forced back towards relief solenoid 126 only if pressure in tubing segment 36a exceeds about 200 mmHg. As a result, relief pad 124 operates as a backup to the pressure relief functions of control pad 120. It will be understood that the forces provide to the solenoids 123 and 126 could be varied as desired. In addition, the relative force levels provided by the solenoids 123 and 126 could be reversed, i.e., relief solenoid 126 could provide lower pressure relief while control solenoid 123 could provide higher pressure relief.

In operation, the control pad 120 is moved into position 120a in close proximity with the exposed portion 36a of outflow line 36 whenever the lever 108 is depressed and the race 116 moves towards the pump head 130. Both solenoids 123 and 126 are powered on when lever 108 reaches its final position locking cassette 40 in place.

Mechanism 146, also moved by the lever 108, moves the plunger 122 of control solenoid 123 towards or away from the segment 36a and, thereby, also moves the control pad 120 between its rearward, or retracted, position and its forward position (indicated at 120a). In the forward position, the control solenoid 123 can act with precision over the best portion of its operating range to compress segment 36a against relief pad 124, thereby regulating fluid flow and pressure at the irrigation site 22. In the rearward position, control pad 120 is retracted from segment 36a so that the cassette 40 can be removed easily.

It will be understood that although the valve assembly described above is particularly advantageous in irrigation systems according to the present invention, it may also be used in any application in which fluid flow is to be restricted using a pinch-type valve operating on a fluid line.

Outflow Tubing Segment

Figure 8B:
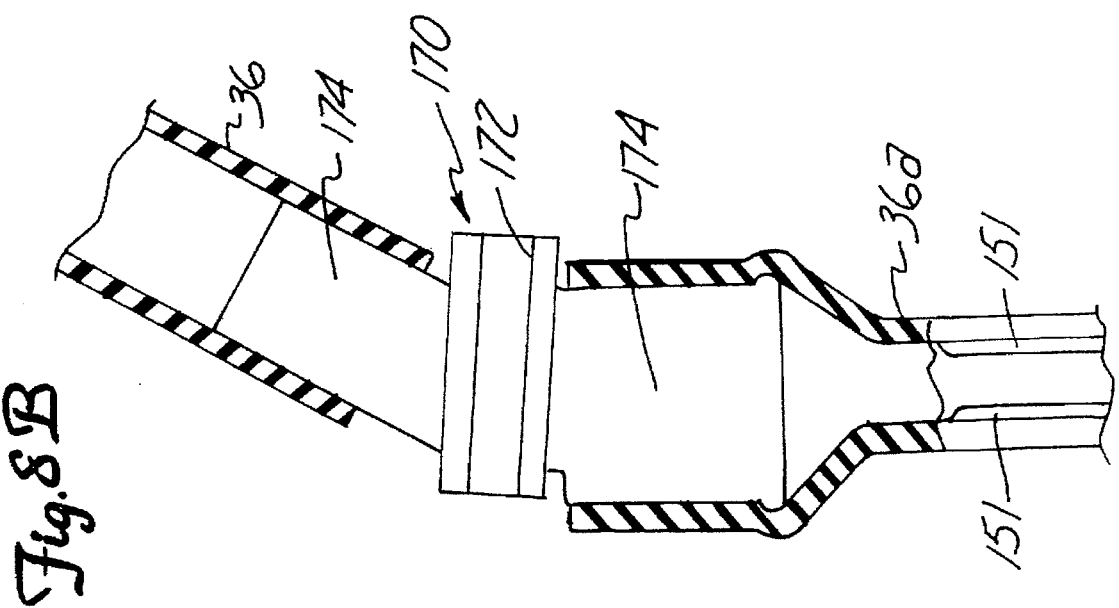
FIG. 8B is a partial view in partial cross-section of the preferred outflow tubing segment and fittings used to connect it to the remainder of the outflow tubing.
Figure 8A:
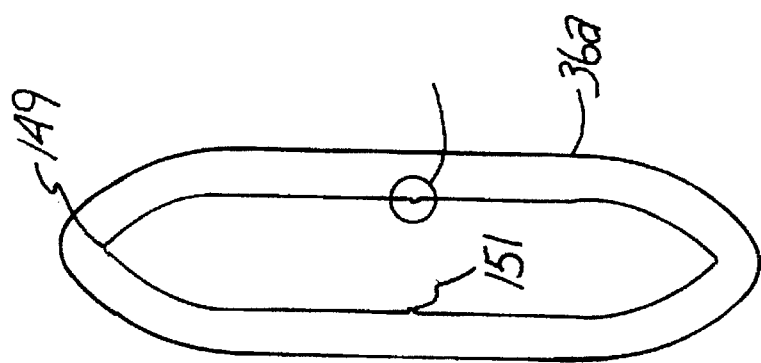
FIG. 8A is a cross-section view of the held portion of the outflow line.

Referring now to FIGS. 8A and 8B, an axial cross-section view of a preferred segment 36a of the outflow line 36 is depicted in 8A while a partial view in partial cross-section of segment 36a is depicted in FIG. 8B. The preferred tubing segment 36a is flattened to enhance control over pressure in the outflow line 36 and, as a result, also at the irrigation site 22. Although the preferred segment 36a takes the profile described below, it will be understood, however, that segment 36a of the outflow tubing line 36 can take many forms including a standard circular cross-sectional shape.

The profile of the preferred segment 36a has interior corners 149, preferably with a radius of less than 0.010 inch, and more preferably with a radius of about 0.001 inch. The wall thickness of the tubing should be thin, preferably between about 0.030 and 0.050 inches and most preferably about 0.040 inches. The wall should be soft, with a durometer of between about 40 to 50 Shore A. An extruded or molded silicone material is preferred, but other low durometer thermoplastics such as polyvinyl chloride may be used.

The preferred profile provides advantages by lowering the occlusion force, i.e., the force needed to close off segment 36a completely. The profile also reduces the tendency of the tubing to form a "dog bone" shaped profile when the tubing is occluded.

The preferred segment 36a may include at least one projection 151 formed in the interior wall surface of the tubing 36a. One preferred projection 151 is seen in greater detail as enlarged in FIG. 9. The projection 151 is provided to prevent the total occlusion of the tubing in the event suction in the outflow line 36 attempts to completely flatten the tube 36a. A radius of between about 0.005 and 0.010 inches is considered preferred for projections 151.

The preferred projections 151 extend generally parallel to the axis of the tubing segment 36a (see FIG. 8B). Although one projection 151 provides some of the benefits described above, it is more preferred to provide at least two projections 151 on opposing sides of the tubing segment 36a. The preferred projections are also offset from each other along the longer transverse axis of the tubing segment 36a, i.e., between opposing interior corners 149. The preferred offset between projections 151 is approximately 0.045 inches.

Referring to the partial view in partial cross-section of FIG. 8B, standard round tubing 36 forming the upstream and downstream portions of outflow line 36 is connected to segment 36a using fittings 170 at each end of the segment 36a (although only one end is shown, it will be understood that the opposing end is similarly constructed). Each fitting 170 includes a pair of nipples 174 which are inserted into the tubing 36 or 36a. Fittings 170 preferably include slots 172 which cooperate with notches 92 in cassette 40 (see FIG. 3) to retain segment 36a in proper position within the valve assembly in fluid control module 24. In the preferred embodiment, segment 36a is held straight within cassette 40 as best seen in FIG. 7. Both tubing segment 36a and standard round tubing 36 are connected to fittings 170 using any suitable method including clamps, adhesives, etc.

It will be understood that although the flattened tubing segment described above is particularly advantageous in tubing sets and irrigation systems according to the present invention, it may also be used in any application in which fluid flow is to be restricted using a pinch-type valve operating on a fluid line.

Pressure Sensing Line Coupling

Referring now to FIG. 10, a detailed cross section view of the interaction between the preferred pressure sensing line fitting 66 contained in the preferred cassette 40 and the preferred pressure sensing port 128 located on fluid control module 24 is illustrated. As discussed above, fitting 66 connects pressure-sensing line 38 to the fluid control module 24 and port 128 completes the line of connection.

The pressure-sensing line 38 preferably terminates in an adapter 150 located loosely within a hole 152 in interior wall 88 of cassette 40. A preferred fitting 66 is attached to one end of the adapter 150, and located within hole 96 in side wall 94. Hole 96 is preferably oversized to allow fitting 66 to move both axially as well as radially within hole 96.

A spring 154 is preferably located between a washer 156 surrounding hole 152 and a flange 158 on the periphery of fitting 66. Spring 154 resiliently biases the fitting 66 towards wall 94 and allows the fitting 66 to "float" within hole 96 in wall 94 of cassette 40. The portion of the side wall 94 immediately adjacent the hole 96 acts as a stop against the flange 158 to limit the axial movement of the fitting 66 under the urging of spring 154.

When the cassette 40 is inserted into the cassette-receiving passageway 98 in fluid control module 24, the fitting 66 contacts port 128. A seal 160, located within a substantially planar region in fitting 66, is pressed against the outer face of port 128 because of the biasing of fitting 66 towards wall 94 (by spring 154 in the preferred embodiment). As a result, fitting 66 and port 128 form a face seal to seal the pressure sensing line 38 with the pressure sensing monitor in the fluid control module 24. Seal 160 can be an O-ring or gasket. Preferably, seal 160 comprises a QUAD-RING® which provides increased sealing abilities.

A length of tubing 162, conveniently fitted over a barb 164, conveys pressure information from pressure sensing line 38 to a pressure transducer in fluid control module 24 so that the valve assembly and motor can be properly controlled to provide the desired pressure in the outflow line 36 and, therefore, at the irrigation site 22.

In the preferred coupling, seal 160 is located at the bottom of an opening which widens to form a frustrum of a cone as indicated at surface 159 as shown in FIG. 10. That construction aids in guiding fitting 66 over port 128 so that the outer face of port 128 is in proper alignment with seal 160.

Alternately, it will be understood that shapes of fitting 66 and port 128 could be switched and still provide the desired guiding function.

Both the corresponding shapes of fitting 66 and port 128 as well as the floating assembly of fitting 66 provide the ability to seal the pressure sensing line 38 with the pressure sensing equipment in fluid control module in spite of misalignment caused during insertion of the cassette into passageway 98 and/or inaccuracies in construction of the cassette 40.

Pressure Control Scheme

In the preferred irrigation system 20 described above, many of the components operate and/or cooperate to maintain the desired fluid pressure and/or flow at the irrigation site 22. As described above, the pump head 130 and race 116 operate on inflow tubing segment 34a to pump fluid towards the irrigation site at a desired flow rate. Flow rate through and fluid pressure at the irrigation site 22 are both at least partially controlled by the speed of pump head 130.

Pressure at the irrigation site and flow rate are also partially controlled by the action of control pad 120 and, more specifically, anvil 121, which compresses against relief pad 124 to restrict flow through the tubing segment 36a. By restricting or allowing outflow from the irrigation site 22, pressure at the irrigation site 22 can be increased or decreased. Likewise, pressure at the irrigation site 22 can also be increased or decreased by changing the speed of the motor 138 driving pump head 130.

The pressure sensing line 38 and corresponding monitoring equipment within fluid control module 24 provide feedback to the system which is used to control the movement of control pad 120 as well as the speed of the pump head 130.

Pressure relief functions are accomplished using the maximum forces provided by the control and relief solenoids 123 and 126 as described in detail above. These functions will typically activate only if the pressure monitoring and control system operating on the pump speed and control pad movement malfunctions.

It is to be understood that even though numerous characteristics and advantages of the present invention have been set forth in the foregoing description, together with details of the structure and function of a preferred embodiment of the invention, the disclosure is illustrative only, and changes may be made in detail, especially in matters of shape, size and arrangement of parts within the principles of the invention to the full extent indicated by the broad general meaning of the terms in which the appended claims are expressed.

We claim:

1. A tubing set for use in an irrigation system of the type comprising a housing having a cassette-receiving passageway, a race mounted on one side of the passageway, a peristaltic pump head mounted on the opposing side of the passageway, and means for moving the race and pump head relative to one another between a pumping position and a release position, wherein in the pumping position the pump head and the race are positioned in close proximity and further wherein in the release position the pump head and the race are positioned distally from one another, the tubing set comprising:

an inflow line for providing irrigation fluid to the internal body irrigation site;

a cassette having a generally arcuate shape, the cassette retaining a portion of the inflow line and including an opening for receiving the pump head and the race on opposing sides of the inflow line, a segment of the portion of the inflow line being exposed within the opening such that the pump head and the race at least partially compress the segment when in the pumping position.

2. The tubing set according to claim 1, further comprising a pressure sensing line, a portion of which is retained by the cassette, the pressure sensing line terminating in a fitting retained by the cassette, wherein the pressure sensing line is adapted to conduct a signal representative of the pressure within the internal body irrigation site to the fitting.

3. The tubing set according to claim 2, wherein the fitting is retained within the cassette, the fitting capable of movement axially and being biased in at least one direction.

4. The tubing set according to claim 3, wherein the fitting forms a face seal with a port provided on the housing.

5. The tubing set according to claim 4, wherein the fitting further comprises a substantially planar region in which a seal is retained.

6. The tubing set according to claim 2, wherein the fitting further comprises means for forming a seal with a port on the housing, the seal being formed without substantial axial movement between the fitting and the port.

7. The tubing set according to claim 6, wherein the means for forming a seal further comprises a face seal between the fitting and the port.

8. The tubing set according to claim 1, further comprising at least one alignment slot and corresponding rib formed in the cassette and housing proximate the cassette-receiving passageway, such that the orientation of the cassette in the passageway is controlled.

9. A tubing set for use in an irrigation system of the type comprising a housing having a cassette-receiving passageway, a race mounted on one side of the passageway, a peristaltic pump head mounted on the opposing side of the passageway, and means for moving the race and pump head relative to one another between a pumping position and a release position, wherein in the pumping position the pump head and the race are positioned in close proximity and further wherein in the release position the pump head and the race are positioned distally from one another, the tubing set comprising:

an inflow line for providing irrigation fluid to the internal body irrigation site;

a cassette having a generally arcuate shape, the cassette retaining a portion of the inflow line, a segment of the portion of the inflow line being exposed such that the pump head and the race at least partially compress the segment when in the pumping position; and an outflow line for draining irrigation fluid from the irrigation site, a portion of the outflow line being retained by the cassette, wherein the portion of the outflow line comprises an exposed segment adapted to be operated on by a valve located proximate the cassette receiving passageway.

10. A tubing set according to claim 9, wherein the exposed segment of the outflow line has a generally flattened shape including a pair of interior corners at opposing ends of a cross-section of the segment.

11. A tubing set according to claim 10, wherein each of the interior corners has a radius of about 0.01 inches or less.

12. The tubing set according to claim 10, wherein each of the interior corners has a radius of about 0.001 inches.

13. The tubing set according to claim 10, wherein the exposed segment further comprises a projection formed in the inner surface of the segment.

14. The tubing set according to claim 13, wherein the projection is linear and extends axially along the segment.

15. The tubing set according to claim 9, further comprising two projections formed in the inner surface of the segment, the projections being formed on opposing sides of the segment.

16. The tubing set according to claim 15, wherein the projections are linear and extend axially along the segment.

17. The tubing set according to claim 16, wherein the projections are offset from each other along a line extending between the interior corners of the segment.

18. A tubing set for use in an irrigation system for providing irrigation fluid to an internal body irrigation site, the system comprising a housing having a cassette-receiving passageway; a valve for controlling pressure at the irrigation site, the valve being positioned proximate the cassette receiving passageway; a port on the housing proximate the passageway, the port in communication a pressure monitor for monitoring pressure at the irrigation site; a race mounted on one side of the passageway; a peristaltic pump head mounted on the opposing side of the passageway; and means for moving the race and pump head relative to one another between a pumping position and a release position, wherein in the pumping position the pump head and the race are positioned in close proximity and further wherein in the release position the pump head and the race are positioned distally from one another, the tubing set comprising:

an inflow line for providing irrigation fluid to the irrigation site;

a cassette retaining a portion of the inflow line, a segment of the portion of the inflow line being exposed such that the pump head and the race at least partially compress the segment when in the pumping position, the cassette having a generally arcuate shape such that the portion of the inflow line retained by the cassette follows a generally arcuate line;

an outflow line for carrying irrigation fluid away from the irrigation site, wherein a portion of the outflow line is retained by the cassette, and further wherein the portion of the outflow line comprises an exposed segment adapted to be operated on by the valve located proximate the cassette-receiving passageway and yet further wherein the exposed segment of the outflow line has a generally flattened shape including a pair of interior corners at opposing ends of a cross-section of the segment;

a pressure sensing line, a portion of which is retained by the cassette, the pressure sensing line terminating in a fitting retained by the cassette, wherein the pressure sensing line conducts a signal representative of the pressure within the irrigation site to the fitting, and further wherein the fitting is capable of movement axially and being biased in at least one direction, and yet further wherein the fitting forms a face seal with the pressure sensing port on the housing.

19. An irrigation system for use in endoscopic procedures for maintaining and controlling flow of irrigation fluid to an internal body irrigation site, the system comprising:

a housing having a cassette-receiving passageway;

a peristaltic pump head attached to the housing on one side of the passageway;

a race attached to the housing on an opposite side of the passageway from the pump head;

means for moving the pump head and race relative to each other between a pumping position and a release position;

a removable tubing set comprising:

an inflow line for providing irrigation fluid to the internal body irrigation site;

a cassette having a generally arcuate shape, the cassette retaining a portion of the inflow line, a segment of the portion of the inflow line being exposed such that the pump head and the race at least partially compress the segment when in the pumping position.

20. The irrigation system according to claim 19, wherein the race is resiliently mounted for limited movement towards and away from the pump head when in the pumping position.

21. The irrigation system according to claim 19, wherein the exposed segment of the outflow line has a generally flattened shape including a pair of interior corners at opposing ends of a cross-section of the segment.

22. The irrigation system according to claim 21, wherein each of the interior corners has a radius of about 0.01 inches or less.

23. The irrigation system according to claim 21, wherein each of the interior corners has a radius of about 0.001 inches.

24. The irrigation system according to claim 21, wherein the exposed segment further comprises a projection formed in the inner surface of the segment.

25. The irrigation system according to claim 24, wherein the projection is linear and extends axially along the segment.

26. The irrigation system according to claim 21, further comprising two projections formed in the inner surface of the segment, the projections being formed on opposing sides of the segment.

27. The irrigation system according to claim 26, wherein the projections are linear and extend axially along the segment.

28. The irrigation system according to claim 27, wherein the projections are offset from each other along a line extending between the interior corners of the segment.

29. The irrigation system according to claim 19, further comprising a pressure sensing line, a portion of which is retained by the cassette, the pressure sensing line terminating in a fitting retained by the cassette, wherein the pressure sensing line is adapted to conduct a signal representative of the pressure within the internal body irrigation site to the fitting.

30. The irrigation system according to claim 29, wherein the fitting is retained within the cassette, the fitting capable of movement axially and being biased in at least one direction.

31. The irrigation system according to claim 29, wherein the fitting forms a face seal with a port provided on the housing.

32. The irrigation system according to claim 31, wherein the fitting further comprises a substantially planar region in which a seal is retained.

33. The irrigation system according to claim 29, wherein the fitting further comprises means for forming a seal with a port on the housing, the seal being formed without substantial axial movement between the fitting and the port.

34. The irrigation system according to claim 33, wherein the means for forming further comprises a face seal between the fitting and the port.

35. The irrigation system according to claim 19, further comprising at least one alignment slot and corresponding rib formed in the cassette and housing proximate the cassette-receiving passageway, such that the orientation of the cassette in the passageway is controlled.

36. An irrigation system for use in endoscopic procedures for maintaining and controlling flow of irrigation fluid to an internal body irrigation site, the system comprising:

a housing having a cassette-receiving passageway;

a peristaltic pump head mounted on one side of the passageway;

a race mounted on an opposite side of the passageway from the pump head;

means for moving the pump head and race relative to each other between a pumping position and a release position:

a removable tubing set comprising:

an inflow line for providing irrigation fluid to the internal body irrigation site;

a cassette having a generally arcuate shape, the cassette retaining a portion of the inflow line, a segment of the portion of the inflow line being exposed such that the pump head and the race at least partially compress the segment when in the pumping position:

a valve located proximate the cassette-receiving passageway; and an outflow line for draining irrigation fluid from the irrigation site, a portion of the outflow line being retained by the cassette, wherein the portion of the outflow line comprises an exposed segment adapted to be compressed by the valve.

37. The irrigation system according to claim 36, wherein the valve comprises a relief pad and an anvil, the exposed segment of the outflow line being located between the relief pad and the anvil, the anvil mounted for movement towards the relief pad to compress the exposed segment.

38. The irrigation system according to claim 37, wherein the anvil is mounted on the plunger of a solenoid.

39. The irrigation system according to claim 37, wherein the relief pad is mounted to move away from the exposed segment when the irrigation fluid pressure in the exposed segment exceeds a predetermined level.

40. The irrigation system according to claim 39, wherein the relief pad is mounted on the plunger of a relief solenoid.

41. An irrigation system for use in endoscopic procedures for maintaining and controlling flow of irrigation fluid to an internal body irrigation site, the system comprising:

a housing having a cassette-receiving passageway;

a peristaltic pump head mounted on one side of the passageway;

a race mounted on an opposite side of the passageway from the pump head, the race being resiliently mounted for limited movement towards and away from the pump head;

means for moving the pump head and race relative to each other between a pumping position and a release position;

an inflow line for providing irrigation fluid to the irrigation site;

an outflow line for carrying irrigation fluid away from the irrigation site;

a valve located proximate the cassette-receiving passageway, the valve comprising a relief pad and an anvil, the outflow line being located between the relief pad and the anvil, the anvil mounted for movement towards the relief pad to compress the outflow line;

a cassette having a generally arcuate shape, the cassette retaining a portion of each of the inflow and outflow lines, wherein a segment of the portion of the inflow line is exposed such that the pump head and the race at least partially compress the segment when in the pumping position, further wherein the portion of the outflow line comprises an exposed segment located between the relief pad and the anvil of the valve, the exposed segment of the outflow line having a generally flattened shape including a pair of interior corners at opposing ends of a cross-section of the segment;

a pressure sensing line, a portion of which is retained by the cassette, the pressure sensing line terminating in a fitting retained by the cassette, wherein the pressure sensing line conducts a signal representative of the pressure within the irrigation site to the fitting, and further wherein the fitting is capable of movement axially and being biased in at least one direction, and yet further wherein the fitting forms a face seal with the pressure sensing port on the housing.

42. An irrigation system for use in endoscopic procedures for maintaining and controlling flow of irrigation fluid to an internal body irrigation site, the system comprising:

an irrigation pump operating on an inflow line supplying irrigation fluid to the irrigation site;

an outflow line carrying irrigation fluid away from the irrigation site;

a valve compressing a segment of the outflow line to restrict outflow from the irrigation site through the outflow line;

the segment of the outflow line compressed by the valve further comprising a generally flattened shape including a pair of interior corners at opposing ends of a cross-section of the segment.

43. The irrigation system according to claim 42, wherein each of the interior corners has a radius of about 0.01 inches or less.

44. The irrigation system according to claim 42, wherein each of the interior corners has a radius of about 0.001 inches.

45. The irrigation system according to claim 42, wherein the exposed segment further comprises a projection formed in the inner surface of the segment.

46. The irrigation system according to claim 45, wherein the projection is linear and extends axially along the segment.

47. The irrigation system according to claim 42, further comprising two or more projections formed in the inner surface of the segment, at least two of the projections being formed on opposing sides of the segment.

48. The irrigation system according to claim 47, wherein the projections are linear and extend axially along the segment.

49. The irrigation system according to claim 47, wherein at least two of the projections are offset from each other along a line extending between the interior corners of the segment.

* * * * *

UNITED STATES PATENT AND TRADEMARK OFFICE
CERTIFICATE OF CORRECTION

PATENT NO. : 5,626,563            Page 1 of 2

DATED : May 6, 1997

INVENTOR(S) : Larry H. Dodge, Ulf B. Dunberger, Thomas D. Egan, Harpreet Kauar and Kenneth E. Merte It is certified that error appears in the above-indentified patent and that said Letters Patent is hereby corrected as shown below:

Title page "Related U.S. Application Data" [63] should only read --Continuation-in-part of Serial No. 3,475, January 12, 1993, Pat. No. 5,403,277--.

Title page "Foreign Application Priority Data" [30] should be deleted as the foreigns listed are counterpart applications that were filed claiming priority from this application.

Col. 1, lines 5-9, "This application continuation of PCT/US94/00563, filed Jan. 12, 1994, which is a continuation-in-part of Ser. No. 08/003,475, filed Jan. 12, 1993, now U.S. Pat. 5,403,277, which is hereby incorporated by reference." should read --This application is a continuation-in-part of Ser. No. 08/003,475, filed Jan. 12, 1993, now U.S. Pat. 5,403,277, which is hereby incorporated by reference.--

Col. 15, line 55, "A" should read --The--.

Col. 15, line 59, "A" should read --The--.

UNITED STATES PATENT AND TRADEMARK OFFICE
CERTIFICATE OF CORRECTION

PATENT NO. : 5,626,563

DATED : May 6, 1997

INVENTOR(S) : Larry H. Dodge, Ulf B. Dunberger, Thomas D. Egan, Harpreet Kauar and Kenneth E. Merte It is certified that error appears in the above-identified patent and that said Letters Patent is hereby corrected as shown below:

Col. 16, line 1, "9" should read --10--.

Signed and Sealed this

Twenty-fourth Day of March, 1998

Attest:

BRUCE LEHMAN

Attesting Officer

Commissioner of Patents and Trademarks